United States Patent [19]

Epting, Jr.

[11] 4,448,770

[45] May 15, 1984

[54] DIETETIC BEVERAGE

[75] Inventor: Elmer E. Epting, Jr., Newberry, S.C.

[73] Assignee: Electroade, Inc., Newberry, S.C.

[21] Appl. No.: 358,845

[22] Filed: Mar. 17, 1982

[51] Int. Cl.$^3$ .................. A61K 31/70; A61K 33/06; A61K 33/14

[52] U.S. Cl. .................. 424/153; 424/154; 424/180

[58] Field of Search .................. 424/180, 153, 154

[56] References Cited

U.S. PATENT DOCUMENTS

| | | | |
|---|---|---|---|
| 2,224,252 | 12/1940 | Callaway | 424/153 |
| 3,337,404 | 8/1967 | Polli et al. | 424/153 |
| 3,657,424 | 4/1972 | Atkins et al. | 424/153 |
| 3,676,553 | 7/1972 | Reynolds | 424/153 |
| 4,312,856 | 1/1982 | Korduner | 424/153 |
| 4,322,407 | 3/1982 | Ko | 424/153 |

*Primary Examiner*—Stanley J. Friedman
*Attorney, Agent, or Firm*—Dority & Flint

[57] ABSTRACT

A dietetic beverage, adapted for consumption by humans to maintain the balance of body fluids during periods of fluid depletion or potassium depletion, comprising an aqueous solution containing per gallon:

30-50 meq of potassium ion
5-10 meq of calcium ion
1-3 meq of magnesium ion
5-10 ounces of sucrose, provided that each of potassium, calcium and magnesium ions is in the form of a soluble salt.

5 Claims, No Drawings

DIETETIC BEVERAGE

DESCRIPTION

1. Technical Field

This invention relates to a beverage for consumption by persons needing fluid and electrolyte replacement during periods of exercise or potassium deficiency.

2. Background Art

It has been proposed by Kahm (U.S. Pat. No. 4,042,684) to provide a dietetic beverage containing sugar, sodium chloride, potassium chloride and citric acid for supplementing sugars and essential salts in a mammalian body, depleted thereof during vigorous physical exercise.

Callaway has proposed (U.S. Pat. No. 2,224,252) an alkaline food product containing sodium, potassium, calcium and magnesium, which product is admixed with various food or drinks. The product is said to correct the acid-base balance of athletes or of people suffering from acidosis.

Polli et al have proposed (U.S. Pat. No. 3,337,404) an effervescent composition, based on potassium chloride, for potassium replacement therapy. The composition also contains citric acid and a soluble sweetener. The effervescense of the composition is said to mask the unpalatable taste normally associated with potassium-containing solutions.

Citrus fruit beverages or concentrates, fortified with various inorganic salts, have been proposed by Aktins et al (U.S. Pat. No. 3,657,424), Sperti, et al (U.S. Pat. No. 3,114,641) and Houghtaling et al (U.S. Pat. No. 3,227,562).

A product marketed as Gatorade ® contains no fruit juice, but is artificially flavored with lemon-lime flavoring and contains glucose, sucrose, citric acid, salt, sodium citrate, sodium phosphate and potassium citrate. The product presently available contains 16 mq of sodium and 3 mq of potassium per ounce.

Hand et al (U.S. Pat. No. 4,154,814) have disclosed a therapeutic chewing gum containing sodium and potassium chlorides, wherein the ratio of NaCl:KCl is at least 3:1.

There is therefore a continuing need for the development of palatable orally-ingestible fluids for use in fluid and potassium replacement, whether the fluid and/or potassium loss is a result of strenuous physical or mental activity, illness or side effects of certain drugs.

It is the object of this invention to provide a palatable beverage for maintaining the body fluid and electrolyte balance in athletes and other persons who have suffered, or would otherwise suffer, from fluid or potassium loss or body-fluid electrolyte imbalance.

DISCLOSURE OF THE INVENTION

This invention relates to a beverage for consumption by humans to maintain the balance of body fluids during periods of fluid depletion or potassium depletion, comprising an aqueous solution containing per gallon:
- 30-50 meq of potassium ion
- 5-10 meq of calcium ion
- 1-3 meq of magnesium ion
- 5-10 ounces of sucrose, provided that each of potassium, calcium and magnesium ions is in the form of a soluble salt.

The compositions of this invention can be consumed by athletes engaged in vigorous activity, or by people working in hot environments, or by people who have suffered fluid or potassium loss as a result of illness or the side effects of drugs. The compositions of this invention supplement normal dietetic requirements for an energy source and for potassium, calcium and magnesium in the body fluids and provide a source of potassium, magnesium and calcium, which are lost by perspiration or excreted in the urine.

Because prompt availability of electrolytes is of importance in maintaining body fluid electrolyte levels of persons who, owing to strenuous exercise or unduly hot ambient conditions, are perspiring freely, the electrolytes appropriate for use in the compositions of this invention must be readily soluble in water. The electroyltes will therefore be absorbed rapidly from the digestive tract of the person drinking the dietetic beverages of this invention.

The major electrolyte in the dietetic beverages of this invention is potassium ion, in an amount of 30-50 meq per gallon of aqueous solution. The potassium ion can be in the form of the chloride, nitrate, sulfate, acetate, lactate, tartrate, benzoate, citrate, or other soluble salt. However, the chloride is preferred, most preferably at a level of 35-45 meq per gallon.

Calcium salts having acceptable solubility in water include the acetate, chloride, gluconate, iodide, lactate, maleate, nitrate and proprionate. The amount of calcium salt is 5-10 meq per gallon. Calcium gluconate or calcium glubionate, also known as Neo-Calglucon ®, manufactured by Dorsey Laboratories, a division of Sandoz, Inc. of Lincoln, Nebr., is preferred. Most preferably, the dietetic beverages of this invention will contain 7-10 meq of calcium gluconate per gallon.

Magnesium ions, in the amount of 1-3 meq per gallon of beverage, are introduced in the form of a soluble salt, such as the acetate, benzoate, chloride, iodide, lactate or nitrate. Magensium chloride is a preferred source of magnesium ions in the beverage of this invention.

The energy source used in the beverages of this invention is sucrose, which is also known as sugar or saccharose. Sucrose is hydrolyzed in the digestive tract to glucose and fructose, which are absorbed into the blood stream and further metabolized. Use of sucrose in the beverages of this invention provides a carbohydrate source which permits release of energy in a slower, but more sustained, fashion than is possible when glucose is used as the principal carbohydrate source.

Inclusion of a flavoring additive is recommended for the beverages of this invention, so as to mask the normally unpalatable taste of potassium chloride or other potassium salt. It will be preferred to use a flavoring which is tart, such as lemon, lime, orange, grape, or grapefruit. Peppermint, spearmint, wintergreen and licorice are examplary of other flavorings which can be used. The amounts of flavoring to be used can be determined by routine testing procedures.

Normally, the beverages of this invention will be made up in advance of use and put in bottles or cans. Inclusion of a preservative to lengthen shelf life is accordingly preferred. Perservatives which are commonly used for canned or bottled beverages include sodium benzoate and/or erythorbic acid. However, any preservative meeting F.D.A. standards can be used. Although the beverages of this invention are essentially free of sodium, it will be understood that inclusion of sodium-containing preservatives and/or flavoring agents, in minor amounts, is within the scope of the present invention.

The beverages of this invention can be consumed, on an as-needed basis, by athletes during strenuous exercise or by persons working in very hot environments. Drinking this beverage will help to prevent stomach or leg cramps, as well as loss of body weight, both of which may otherwise occur. It is thought that these beneficial results are a consequence both of electrolyte and fluid replacement in general and of the high potassium content of these beverage. In addition, the beverages of this invention provide a source of energy.

BEST MODE FOR CARRYING OUT THE INVENTION

In a most preferred embodiment, the beverages of this invention will be those comprising 35–45 meq of potassium chloride 7–10 meq of calcium gluconate, 1–3 meq of magnesium chloride and 7–10 ounces of sucrose per gallon and containing a flavoring agent and a preservative.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

A dietetic beverage was prepared from one gallon of water, to which was added 40 meq of potassium chloride, 8 meq of calcium gluconate (Glucobionate), 2 meq of magnesium chloride and 8 ounces of sucrose. Flavoring was added to the homogeneous mixture, along with a trace of stabilizer.

EXAMPLE 2

A beverage is made in similar fashion, which contains per gallon of water: 37 meq of potassium chloride, 9 meq of calcium gluconate, 2.5 meq of magnesium chloride and 9 ounces of sucrose.

EXAMPLE 3

A dietetic beverage was prepared from one gallon of water, to which was added 40 meq of potassium chloride, 8 meq of glubionate calcium, 2 meq of magnesium chloride and 8 ounces of sucrose. Flavoring was added to the homogeneous mixture, along with a trace of stabilizer.

The preceding examples can be repeated with similar success by substituting the generically or specifically described ingredients of this invention for those used in the preceding examples.

From the foregoing description, one skilled in the art can easily ascertain the essential characteristics of this invention and, without departing from the spirit or scope thereof, can make various changes and modifications of the invention to adapt it to various usages and conditions.

I claim:

1. A beverage, essentially free of sodium ions, for consumption by humans to maintain the balance of body fluids during periods of fluid depletion or potassium depletion, comprising an aqueous solution, contain per gallon:

30–50 meq of potassium chloride
   5–10 meq of calcium gluconate or glubionate calcium
   1–3 meq of magnesium chloride
   5–10 ounces of sucrose, and
   provided further that the beverage composition contains no sodium ion except that present in minor amounts in flavoring agents, preservatives, or other minor additives.

2. The beverage of claim 1, which also contains a flavoring additive.

3. The beverage of claim 1, which also contains a preservative.

4. The beverage of claim 1, which comprises 35–45 meq of potassium chloride, 7–10 meq of calcium gluconate, 1–3 meq of magnesium chloride and 7–10 ounces of sucrose per gallon and which contains a flavoring agent and a preservative.

5. The beverage of claim 1, which comprises 35–45 meq of potassium chloride, 7–10 meq of glubionate calcium, 1–3 meq of magnesium chloride and 7–10 ounces of sucrose per gallon and which contains a flavoring agent and a preservative.

* * * * *